(12) United States Patent
Yanagihara

(10) Patent No.: US 10,172,883 B2
(45) Date of Patent: Jan. 8, 2019

(54) METHODS AND COMPOSITIONS FOR TREATING AND/OR INHIBITING TOXINS USING COPPER-CONTAINING COMPOUNDS

(71) Applicant: ALATALAB SOLUTIONS, LLC, Honolulu, HI (US)

(72) Inventor: Angel A. Yanagihara, Honolulu, HI (US)

(73) Assignee: ALATALAB SOLUTION, LLC, Honolulu, HI (US)

( * ) Notice: Subject to any disclaimer, the term of this patent is extended or adjusted under 35 U.S.C. 154(b) by 0 days.

(21) Appl. No.: 15/317,935

(22) PCT Filed: Jun. 9, 2015

(86) PCT No.: PCT/US2015/034974
§ 371 (c)(1),
(2) Date: Dec. 9, 2016

(87) PCT Pub. No.: WO2015/191639
PCT Pub. Date: Dec. 17, 2015

(65) Prior Publication Data
US 2017/0119817 A1    May 4, 2017

Related U.S. Application Data

(60) Provisional application No. 62/010,330, filed on Jun. 10, 2014.

(51) Int. Cl.
| A61K 33/34 | (2006.01) |
| A61K 9/00 | (2006.01) |
| A61K 45/06 | (2006.01) |
| A61K 47/18 | (2017.01) |

(52) U.S. Cl.
CPC ............ *A61K 33/34* (2013.01); *A61K 9/0014* (2013.01); *A61K 45/06* (2013.01); *A61K 47/18* (2013.01)

(58) Field of Classification Search
CPC ..................................... A61K 33/34
USPC ....................................... 514/171
See application file for complete search history.

(56) References Cited

U.S. PATENT DOCUMENTS

| 4,444,751 A | 4/1984 | Cripps |
| 5,788,952 A | 8/1998 | Gers-Barlag |
| 5,958,397 A | 9/1999 | Smerbeck |
| 6,132,747 A | 10/2000 | Lotan |
| 6,217,885 B1 | 4/2001 | Roder |
| 6,338,837 B1 | 1/2002 | Lotan |
| 6,406,709 B1 | 1/2002 | Lotan |
| 6,375,976 B1 | 4/2002 | Roden |
| 6,696,396 B1 | 2/2004 | Arneson |
| 7,081,247 B2 | 7/2006 | Lotan |
| 7,118,760 B2 | 10/2006 | Gonzalez |
| 2001/0031744 A1 | 10/2001 | Kosbab |
| 2002/0182239 A1 | 12/2002 | Lotan |
| 2004/0170701 A1* | 9/2004 | Carter ................. A61K 31/375 424/638 |
| 2004/0247635 A1 | 12/2004 | Igarashi |
| 2005/0002974 A1 | 1/2005 | Filbry |
| 2005/0037044 A1 | 2/2005 | Yarbrough |
| 2006/0039933 A1 | 2/2006 | Cram |
| 2007/0166411 A1 | 7/2007 | Anthony |
| 2007/0190175 A1 | 8/2007 | Cummins |
| 2007/0212331 A1 | 9/2007 | Baldassare |
| 2007/0269499 A1 | 11/2007 | Hen |
| 2007/0280926 A1 | 12/2007 | Ceko |
| 2008/0138417 A1 | 6/2008 | Grigsby |
| 2008/0274209 A1 | 11/2008 | Smith |
| 2010/0010085 A1 | 1/2010 | Grayson |
| 2010/0034768 A1 | 2/2010 | Castillo |
| 2010/0234454 A1 | 9/2010 | Cuypers |
| 2011/0135763 A1 | 6/2011 | Fish |
| 2013/0078317 A1 | 3/2013 | Yanagihara |
| 2014/0248374 A1* | 9/2014 | Yanagihara .......... A61K 31/325 424/638 |

FOREIGN PATENT DOCUMENTS

| AU | 200248859 | 8/2002 |
| DE | 102009046697 | 5/2011 |
| EP | 2363135 | 9/2011 |
| EP | 2380577 | 10/2011 |
| FR | 2950254 | 3/2011 |
| GB | 1403062 | 8/1975 |
| WO | WO-1998/033494 | 8/1998 |
| WO | WO-1998/053807 | 12/1998 |
| WO | WO-2000/028817 | 5/2000 |
| WO | WO-2000/048578 | 8/2000 |
| WO | WO-2001/037778 | 5/2001 |
| WO | WO-2003/096993 | 11/2003 |
| WO | WO-2005/076731 | 8/2005 |
| WO | WO-2006/133134 | 12/2006 |
| WO | WO 2012/112230 A2 | 8/2012 |

OTHER PUBLICATIONS

Badre, Toxicon 91 (2014) 114e125.*
Lopez, Trends in Immunology, Aug. 2012, vol. 33, No. 8, 406-412.*
International Search Report and Written Opinion for PCT Application No. PCT/US2015/034974, dated Nov. 2, 2015, 12 pages.
Winkel et al.; Jellyfish Antivenoms: Past, present and Future; J. Toxicol. Toxin Revs. vol. 22, No. 1, pp. 115-127 (2003) Abstract, p. 123 Table 1.
Yanagihara et al.; Cubozoan venom-induced cardiovascular collapse; PLOS ONE; vol. 7 No. 12; e51368; Dec. 12, 2012 (Dec. 12, 2012) Abstract.
Bashford et al., "Sequential onset of permeability changes in mouse ascites cells induced by Sendai virus", Biochem. Biophys. Acta, 1985, 814:247-255.

(Continued)

*Primary Examiner* — Nizal S Chandrakumar
(74) *Attorney, Agent, or Firm* — Foley & Lardner LLP

(57) ABSTRACT

The invention described herein is directed to copper-containing compounds for the treatment of toxin exposure (including pore-forming toxin exposure) in a subject in need thereof. The invention is further directed to methods of treating toxin exposure in a subject in need thereof.

10 Claims, 7 Drawing Sheets

(56) References Cited

OTHER PUBLICATIONS

Bashford, C.L., "Membrane Pores—From Biology to Track-Etched Membranes", Bioscience Reports, 1995, 15(6):553-565.
Bernheimer et al., "Interactions between membranes and cytolytic peptides", Biochim Biophys Acta, 1986, 864:123-141.
Bhakdi, S. and Tranum-Jensen, J., "Membrane damage by channel-forming proteins: staphylococcal alpha-toxin, streptolysin-0 and the C5b-9 complement complex", Biochemical Society Symposium, 1985, 50:221-233.
Bjerre et al., "Simultaneous detection of porcine cytokines by multiplex analysis: development of magnetic bioplex assay", Veterinary Immunology and Immunopathology, 2009, 130(1-2):53-58.
Borsos et al., "Lesions in erythrocyte membranes caused by immune haemolysis", Nature, 1964, 202:251-252.
Gilbert, R.J.C., "Pore-forming toxins", Cellular and Molecular Life Sciences CMLS, 2002, 59(5):832-844.
Hessigner, D.A. and Lenhoff, H.M., "Assay and properties of the hemolysis activity of pure venom from the nematocysts of the acontia of the sea anemone Aiptasia pallida", Archives of Biochemistry and Biophysics, 1973, 159(2):629-638.
Bashford et al., "Membrane damage by hemolytic viruses, toxins, complement, and other cytotoxic agents: A common mechanism blocked by divalent cations", J. Biol. Chem., 1986, 261:9300-9308.
Chung et al., "Partial purification and characterization of a hemolysin (CAH1) from Hawaiian box jellyfish (*Carybdea alata*) venom", Toxicon 39, 2001, 981-990.
Escobar-Chávez et al., "Electroporation as an Efficient Physical Enhancer for Skin Drug Delivery", J Clin. Pharm, 2009, 49:1262-1283.
NDC Product Code 43074-114 (Phillips Company), "Advanced Jellyfish Sting Kit (zinc acetate) powder, for suspension," Retrieved from: http://dailymed.nlm.nih.gov/dailymed/druginfo.cfm?id=37811. (5 pages).
Undercurrent, "Two Inexpensive Weapons against Jellyfish Stings," Undercurrent vol. 22, No. 3, <https://www.undercurrent.org/UCnow/dive_magazine/2007/InexpensiveWeapons200703.html>, Mar. 2007, p. 1 -2.
Young et al., "The ninth component of complement and the pore-forming protein (perforin 1) from cytotoxic T cells: structural, immunological, and functional similarities," Science, 1986, 233:184-190.

* cited by examiner

METHODS AND COMPOSITIONS FOR TREATING AND/OR INHIBITING TOXINS USING COPPER-CONTAINING COMPOUNDS

BACKGROUND OF THE INVENTION

Cnidarian phylum members, including sessile anthozoa (anemone, corals), and the medusozoa sub phylum classes such as scyphozoa (common jellyfish) and cubozoa (tropical cuboidal jellies with venoms that result in high morbidity and mortality), are venomous sea life that sting hundreds of thousands of beach goers every year. For example, numerous life-threatening *Chironex fleckeri* and other cubozoan envenomations occur during summer months in North Queensland, Australia northward to Thailand. Symptoms of cnidarian stings include pain, wheals, urticarial, itching, swelling, tingling/numbness, nausea and vomiting, headache, muscle and joint problems, weakness/dizziness, fever, loss of consciousness, respiratory insufficiency, and heart problems. In some cases, infections and/or scarring or skin discoloration also occur. Current treatments are primarily directed at relief of symptoms or, in serious cases, support of cardiovascular integrity after envenomation. A few currently available "Sting Relief" type sprays are typically comprised of non-specific and or locally acting ingredients such as vinegar, lidocaine, papain, aloe, eucalyptus oil, and menthol. Nevertheless, over 100 people are estimated to die each year from cnidarian stings. There remains a need for effective therapies for such stings.

Fire ants sting millions of people per year. Fire ant stings are painful and can be deadly, particularly to small animals. There are currently no effective treatments for the root cause of ant venom pain and inflammation. Treatments are solely designed to address downstream symptoms of the stings. Furthermore, the composition of fire ant venom has not been well-understood, making treatment of bites more challenging. There remains a need for effective therapies for such stings.

SUMMARY OF THE INVENTION

Embodiments described herein generally relate to compositions and methods of treating illnesses, diseases, and conditions associated with exposure to toxins, including but not limited to pore-forming toxins. Such toxin exposure can occur due to stings from certain animals and/or exposure to certain pathogens.

Some embodiments are directed to compositions and methods for treating or alleviating problems associated with exposure to pore-forming toxins. A problematic and rapidly-acting constituent of both cnidarian venom and fire ant venom is pore-forming toxins, or porins. Porins represent an ancient and conserved toxic exudate of most pathogenic bacteria, including *Staphylococcus, Streptococcus, Bacillus* (e.g., anthrax), *Clostridium*, and *E. coli*, and are a major constituent of many marine as well as insect, elapid and viper venoms, including the venoms of ants, bees, and certain spiders and snakes. Potent membrane disruptive porins allow the evasion of host phagocytosis in bacterial infection, or result in rapid prey cytolysis after envenomation. They constitute a fundamental mechanism for infection and prey capture. Thus, effective therapies for treatment of cnidarian envenomations will have general applicability to other conditions associated with pore-forming toxins (PFTs), as well as broad applicability to pathologies resulting from other membrane perturbants (MPs).

The current invention generally relates to compositions for and treatment of PFT-induced disease, illness, syndrome or condition in a patient suffering therefrom. In some aspects, the compositions and therapies can reduce the morbidity and mortality of PFT-induced situations, and can specifically prevent, reduce or inhibit local inflammation and burning pain, as well as systemic and cardiovascular outcomes in such conditions, including for example, cnidarian and ant envenomations as well as the other types described above and elsewhere herein.

Porin insertion into a cell membrane compromises membrane permeability by reducing the barrier function of the cell membrane (Bashford, et al. 1985. "Sequential onset of permeability changes in mouse ascites cells induced by Sendai virus" *Biochim. Biophys. Acta* 814:247-255; Bashford, et al. 1986. "Membrane damage by hemolytic viruses, toxins, complement, and other cytotoxic agents: A common mechanism blocked by divalent cations" *J. Biol. Chem.* 261: 9300-9308). Porin insertion results in fully functional pores that evoke rapid and non-specific membrane depolarization due to passage of monovalent and divalent ions through the newly formed pores. Specifically, efflux of $K^+$, influx of $Na^+$, influx of $Ca^{2+}$ and efflux of $Cl^-$ together result in depolarization of the cells as the internal and external ionic solutions rapidly equilibrate. At the same time, water infusion into the cell results in cell swelling and the distension of pores such that larger molecules, such as intermediates of metabolism (e.g., nucleotides and sugar phosphates), are released. The cascade results in a catastrophic loss of cellular function and cell death, known as pyroptosis. Porin-based cytolysis of red blood cells (RBCs) results in the rapid and potentially lethal loss of $K^+$ and then large tetrameric hemoglobin or hemolysis. Cytolysis of other cell types results in the massive release of lysosomal enzymes, which results in proximal cell lysis of envenomation site dermal cells, nerves and dermal mast cells as well as capillary white blood cells, which in turn massively release potent inflammatory mediators (chemokines and cytokines) with systemic effects. Taken together these events result in local nerve and tissue necrosis, as well as profound pain and both local and systemic inflammation.

All cubozoan venoms studied to date, including *Chironex fleckeri* venom, contain extremely potent and rapid acting pore-forming toxins. Although post mortem examinations of cubozoan victims have not consistently demonstrated lethal levels of hemolysis, it has been discovered that a catastrophic hyperkalemic state with pulseless electrical activity (PEA) precedes clinically measurable hemolysis, and furthermore, that this catastrophic hyperkalemic state is specifically caused by the cubozoan venom PFTs (Yanagihara A, Shohet R V (2012) Cubozoan Venom-Induced Cardiovascular Collapse Is Caused by Hyperkalemia and Prevented by Zinc Gluconate in Mice. *PLoS ONE* 7(12): e51368. doi:10.1371/journal.pone.0051368, which is incorporated herein by reference in its entirety for its methods and compositions, and all other disclosure; in some embodiments, one or more of its methods, compositions, materials and other disclosure can be specifically excluded from the instant methods and compositions). In addition, stings caused by cubozoans can result in significant burning pain, as well as markedly obvious hemolysis at the sting site. In some aspects, embodiments herein relate to effective therapies to reduce the morbidity and mortality outcomes for cnidarian envenomations, which include addressing inflammation, burning pain, and systemic and cardiovascular outcomes.

Zinc-containing compounds have been shown to be effective for inhibiting PFT-induced hyperkalemia, hemolysis and other symptoms, both alone and in combination with other ingredients. U.S. Patent Application Publication No. 2013/0078317 describes the use of zinc-containing compounds for treatment of PFT-induced disease or illness. PCT Publication No. PCT/US2012/000095 describes the treatment of PFT-induced disease or illness with a combination of zinc gluconate and copper gluconate. Both of these applications are incorporated herein by reference in their entireties. The particular classes and species of compositions and methods described in those applications can be explicitly excluded or disclaimed from some embodiments of the instant technology. For example, the instant compositions and methods according to some embodiments can expressly exclude the use of zinc gluconate (or other zinc containing compounds). Pore-forming toxins exhibit general classes of conserved structural homology, some of which appear to require calcium for self-assembly polymerization to form functional transmembrane pores. Thus, some divalent cations, such as, for example, $Zn^{2+}$, $Cu^{2+}$, and $Mg^{2+}$, may be able to competitively bind to calcium binding sites and inhibit self-assembly of calcium dependent porin proteins to form functional polymeric pores. Zinc has also been shown to exhibit membrane-protective effects in the presence of membrane-disruptive molecules and toxins broadly classified as MPs.

In some embodiments, the current invention is predicated, in part, on the surprising discovery that copper gluconate alone is significantly more effective at reducing venom-induced cell hemolysis than zinc gluconate alone or in combination with copper gluconate. While zinc can have some efficacy for treatment of PFT-induced reactions, in some cases the use of zinc to treat many types of PFT-induced reactions also can be problematic due to the presence of zinc-activated pathogenic phospholipases and or zinc-dependent metalloproteinases in some venom and bacteria. Application of zinc-containing compounds in such situations may increase the activity of the phospholipases and or the metalloproteases and thus may increase tissue damage and/or pain associated with the infection or envenomation. Zinc-containing compounds can potentially induce RBC aggregation in stacks to form a rouleaux.

In one aspect, the present invention is directed to a composition comprising an effective amount of a copper-containing compound to treat exposure to a toxin in a subject, including exposure to a pore-forming toxin in a subject. In one embodiment, the copper-containing compound is present at a concentration of greater than about 10 µM. In one embodiment, the composition does not comprise a zinc-containing compound. In one embodiment, the composition further comprises at least one of lactulose, magnesium, and urea. In a preferred embodiment, the composition comprises urea.

In one embodiment, the copper-containing compound comprises a non-toxic counter-ion to copper in a copper salt. In one embodiment, the non-toxic counter-ion is pharmaceutical grade (USP) gluconate, chloride, glycinate or sulfate. In one embodiment, the composition further contains D-lactulose, glucose, lactose, galactose, sucrose, pentose, fructose, polymer (e.g., polyvinyl alcohol), or a complex polyanion. In a preferred embodiment, the copper-containing compound is copper gluconate (USP). In one embodiment, the copper-containing compound is elemental copper.

The composition may be formulated for topical, oral or intravenous administration. In one embodiment, the composition is formulated for topical administration. In one embodiment, the topical formulation comprises urea. In one embodiment, the composition is formulated for intravenous administration. In one embodiment, the composition is formulated for transdermal administration. In one embodiment, the composition does not comprise vinegar.

In one embodiment, the composition comprises triamcinolone acetonide. In one embodiment, the composition comprises diphenhydramine. In one embodiment, the composition comprises lidocaine.

In one aspect, the present invention is directed to a method for treating exposure to a toxin, including without limitation, exposure to a pore-forming toxin, in a subject, comprising administering to the subject a therapeutically effective amount of the composition described herein, wherein a symptom or condition of the exposure is treated. In one embodiment, the pore forming toxin is from cnidarian venom, coral venom, insect venom, animal venom, plant toxin, or a pathogenic fungi, mold, virus or bacterium. In one preferred embodiment, the toxin is from a jellyfish. In another preferred embodiment, the toxin is from a fire ant. In yet another preferred embodiment, the toxin is from a pathogenic fungi, mold, virus or bacterium.

In one embodiment, the composition is administered topically. In one embodiment, the topical formulation comprises urea. In one embodiment, the composition is administered intravenously. In one embodiment, the composition is administered transdermally.

In some embodiments of the invention, PFT-related illnesses and conditions can include, without limitation, hemolytic and inflammatory dermal responses, acute point pain and swelling at the site of a PFT sting, hyperkalemia, hypovolemia, hypocalcemia, toxic calcium influx, hemolysis, excessive cytokine and histamine release, Irukandji syndrome, catecholamine surge, bacterial infection and or sepsis, viral hemorrhagic septicemia, mold associated mycotoxin toxicity, cardiovascular collapse, and/or pulseless electrical activity (PEA). In some embodiments of the invention, PFT-related illnesses and conditions can include, without limitation, envenomation by cnidarians with cardiovascular collapse, respiratory distress, inflammation and/or Irukandji syndrome. For example, severe envenomations by the Carybdeidae family (four-tentacled cubozoan members of the cnidarian phylum) can lead to Irukandji syndrome, which is associated with "catecholamine surge" and "cytokine storm" type symptoms that include pain, sweating, acute anxiety, and life-threatening cardiovascular effects.

Additional conditions include diseases, illnesses or syndromes associated with porin-mediated cell and tissue damage, including, but not limited to, those resulting from a bacterial infection, a viral infection, a fungal infection or exposure to mold, reaction to insect stings and arachnid and snake bites, and reactions to stings from organisms within the cnidarian phylum.

DETAILED DESCRIPTION OF THE INVENTION

Figure 1:
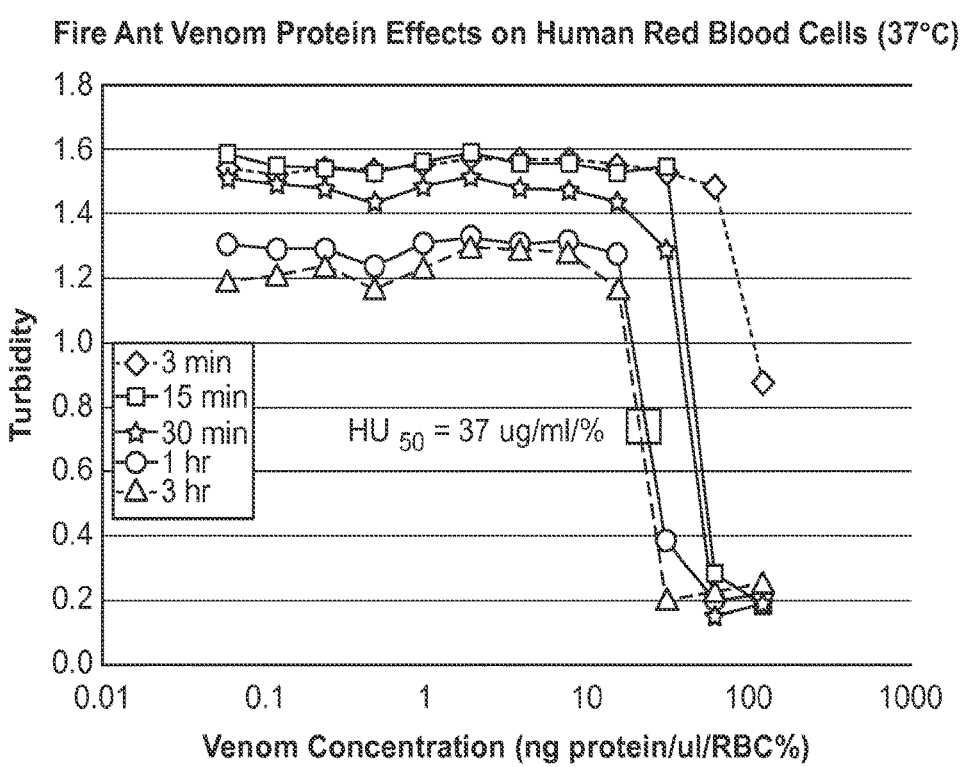
FIG. 1 is a depiction of the hemolytic activity of fire ant venom protein.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

Definitions

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "treat," "treating," or "treatment" as used herein are defined as acting upon a disease, disorder, or condition with an agent to reduce or ameliorate harmful or any other undesired effects of the disease, disorder, or condition and/or its symptoms. For purposes of this invention, beneficial or desired results include, but are not limited to: treating one or more symptoms of contact with a toxin, e.g. pore-forming toxin.

As used herein, the term "patient" or "subject" refers to a mammal. In a preferred embodiment, the subject is a human.

Compositions of the Invention

The term "non-toxic counter-ion" refers to any ion that is associated with the metal ion (e.g., copper) that is non-toxic when administered to a subject. In some embodiments, the non-toxic counter-ion is any sugar-based counter-ion, including, but not limited to, gluconate, chloride, or sulfate. In some embodiments, the copper-containing compound is copper gluconate. In some embodiments, the composition comprises elemental copper. In one embodiment, one or more specific non-toxic counter ions is excluded from the composition. In one embodiment, the composition does not comprise elemental copper.

In some embodiments, the counter-ion can be any ion selected for its property in meeting a desire to 1) avoid placing an additional ionic load in the plasma and/or 2) avoid burdening the kidney clearance load of a subject afflicted by a porin-mediated disease or condition. Applicable counter-ions that meet these criteria will be apparent to a person of ordinary skill in the art.

In one aspect, the present invention is directed to a composition comprising an effective amount of a copper-containing compound to treat exposure to a toxin, including without limitation, pore-forming toxin in a subject. The toxin (including the pore-forming toxin) may be from any source. In one embodiment, the toxin is from a Cnidarian family member, for example and without limitation an anthozoan (anemone, corals), a hydrozoan, a scyphozoan (common jellyfish), or a cubozoan (tropical cuboidal jellyfish). In one embodiment, the toxin is from Chirodropidae (e.g. *Chironex fleckeri, Chiropsalmus quadrumanus*) or Carybdeidae (e.g. *Carukia barnesi, Malo maxima, Carybdea alata, Alatina moseri*). Pore-forming toxins have been found in all members of the cnidarian phylum that have been examined including, for example, in hydrozoans such as *Physalia* sp., stinging hydroid, scyphozoans, stinging nettles, lion's mane and anthozoans such as anemones, coral and fire coral.

In one aspect, the toxin (e.g., pore-forming toxin) is from a pathogenic bacterium, for example and without limitation a *Staphylococcus*, a *Clostridium*, a *Streptococcus*, a *Bacillis*, an *Aeromonas*, an *Escherichia*, or a *Neisseria*. In one embodiment, the bacterium is *Bacillus anthracis*. In one embodiment, the bacterium is *E. coli*. In one embodiment, the bacterium is *S. aureus*. In one embodiment, the bacterium is *C. perfringens*. In one embodiment, the bacterium is *S. pneumonia*. In one embodiment, the bacterium is *A. hydropohila*. In one embodiment, the bacterium is *C. lacteus*. In one embodiment, the bacterium is *B. thuringiensis*.

In one aspect, the toxin (e.g., pore-forming toxin) is from a virus. Non-limiting examples of viruses known to form divalent cation-sensitive pores include Sendai, Newcastle Disease, and Influenza.

In one aspect the pore forming toxin is a mycotoxin produced by a fungus or mold. Non-limiting examples of molds known to release mycotoxins include black mold, *Exserohilum rostratum, Aspergillus fumigatus* and *Cladosporium* species.

In one aspect, the toxin (e.g., pore-forming toxin) is from an insect, arachnid, elapid or viper. In one embodiment, the pore-forming toxin is from a fire ant (e.g., *Solenopsis invicta, Solenopsis daguerrei, Solenopsis fugax, Solenopsis geminate, Solenopsis molesta, Solenopsis richteri, Solenopsis saevissima, Solenopsis silvestrii, Solenopsis solenopsidis, Solenopsis wagneri, Solenopsis xyloni*, etc.). In one embodiment, the toxin (e.g., pore-forming toxin) is from a bee (e.g., honey bee). In one embodiment, the toxin (e.g., pore-forming toxin) is from a spider. In one embodiment, the toxin (e.g., pore-forming toxin) is from an elapid or viper.

In one aspect, the toxin (e.g., pore-forming toxin) is from a member of the family of pore-forming mushroom toxins. Exemplary toxins in this family include, but are not limited to, phallolysin, flammutoxin, ostreolysin, and the cytolytic proteins identified in Berheinmer (Bernheimer, A. W., and B. Rudy. 1986. *Biochim Biophys Acta* 864:123-141, which is incorporated herein by reference in its entirety).

Other medically relevant toxin- or porin-mediated conditions or sources of porin exposure will be apparent to a person of ordinary skill in the art.

In one aspect, the copper-containing compound is present in the composition in an amount effective for treatment of exposure to the toxin. In one embodiment, the composition comprises about 1 µM to about 100 mM of the copper-containing compound. In one embodiment, the composition comprises at least about 1 µM of the copper-containing compound. In one embodiment, the composition comprises at least about 2 µM of the copper-containing compound. In a preferred embodiment, the composition comprises at least about 3 µM of the copper-containing compound. In one embodiment, the composition comprises at least about 4 µM of the copper-containing compound. In one embodiment, the composition comprises at least about 5 µM of the copper-containing compound. In one embodiment, the composition comprises at least about 10 µM of the copper-containing compound. In one embodiment, the composition comprises at least about 20 µM of the copper-containing compound. In one embodiment, the composition comprises at least about 30 µM of the copper-containing compound. In one embodiment, the composition comprises at least about 40 µM of the copper-containing compound. In one embodiment, the composition comprises at least about 50 µM of the copper-containing compound. In one embodiment, the composition comprises at least about 100 µM of the copper-containing compound. In one embodiment, the composition comprises at least about 250 µM of the copper-containing compound. In one embodiment, the composition comprises at least about 500 µM of the copper-containing compound. In one embodiment, the composition comprises at least about 1 mM of the copper-containing compound. In one embodiment, the composition comprises at least about 10 mM of the copper-containing compound. In one embodiment, the composition comprises at least about 100 mM of the copper-containing compound. Acceptable amounts include ranges and amounts within the recited ranges, including endpoints.

In one embodiment, the copper-containing compound is present in a range of about 0.0005% to about 50% (w/v) of the composition. In one embodiment, the copper-containing compound is present at a concentration of about 0.0005% to about 5% (w/v) of the composition. In one embodiment, the copper-containing compound is present at a concentration of about 0.0005% to about 2% (w/v) of the composition. In one embodiment, the copper-containing compound is present at a concentration of about 0.001% to about 1% (w/v) of the composition. In one embodiment, the copper-containing compound is present at a concentration of about 0.01% to about 1% (w/v) of the composition. In one embodiment, the copper-containing compound is present at a concentration of about 0.1% to about 1% (w/v) of the composition. In one embodiment, the copper-containing compound is present at a concentration of greater than about 0.0005% (w/v). In one embodiment, the copper-containing compound is present at a concentration of about 0.001% (w/v). In one embodiment, the copper-containing compound is present at a concentration of about 0.0015% (w/v). In one embodiment, the copper-containing compound is present at a concentration of about 0.002% (w/v). In one embodiment, the copper-containing compound is present at a concentration of about 0.005% of the composition (w/v). In one embodiment, the copper-containing compound is present at a concentration of about 0.01% of the composition (w/v). In one embodiment, the copper-containing compound is present at a concentration of about 0.01% of the composition (w/v). In one embodiment, the copper-containing compound is present at a concentration of about 0.05% of the composition (w/v). In one embodiment, the copper-containing compound is present at a concentration of about 0.1% of the composition (w/v). In one embodiment, the copper-containing compound is present at a concentration of about 0.5% of the composition (w/v). In one embodiment, the copper-containing compound is present at a concentration of about 1% of the composition (w/v). The amount can be any point within these ranges, as well as any endpoint or range within the given ranges. Acceptable amounts include ranges and amounts within the recited ranges, including endpoints.

In one embodiment, the composition comprises at least one pharmaceutically-acceptable excipient and/or carrier. In one embodiment, the composition comprises at least one other active ingredient. In one embodiment, the composition does not comprise a zinc-containing compound. In one embodiment, the composition comprises at least one of lactulose, magnesium, and urea. In one embodiment, the formulation comprises urea. In one embodiment, the formulation comprises vinegar. In one embodiment, the formulation comprises Hawaiian soapberry aqueous extract. In one embodiment, the formulation comprises lanolin. In one embodiment, the formulation does not comprise vinegar.

As used herein, "pharmaceutically acceptable carrier" and "carrier" generally refer to a non-toxic, inert solid or non-inert, semi-solid or liquid filler, diluent, encapsulating material or formulation auxiliary of any type. Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil; kukui nut oil, camphor oil; and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; and phosphate buffer solutions, as well as other non-toxic compatible lubricants such as sodium lauryl sulfate and magnesium stearate, as well as coloring agents, releasing agents, coating agents, sweetening, flavoring, menthol and perfuming agents, preservatives and antioxidants can also be present in the composition, according to the judgment of the formulator.

The pharmaceutically acceptable carriers described herein, for example, vehicles, adjuvants, excipients, or diluents, are well-known to those who are skilled in the art. Typically, the pharmaceutically acceptable carrier is chemically inert to the therapeutic agents and has no detrimental side effects or toxicity under the conditions of use. The pharmaceutically acceptable carriers can include polymers and polymer matrices, nanoparticles, microbubbles, and the like.

The therapeutic treatment can further comprise inert diluents such as water or other solvents, solubilizing agents and emulsifiers such as ethyl alcohol, isopropyl alcohol, ethyl carbonate, ethyl acetate, benzyl benzoate, propylene glycol, 1,3-butylene glycol, dimethylformamide, oils (in particular, cottonseed, groundnut, corn, germ, olive, castor, and sesame oils), glycerol, polyethylene glycols and fatty acid esters of sorbitan, and mixtures thereof.

Polymerizing agents, such as, for example, polyvinyl alcohols are also contemplated for inclusion in compositions and formulations as disclosed herein.

The composition may be formulated for administration by any route. In one embodiment, the composition is formulated for topical administration. In one embodiment, the composition is formulated for intravenous administration. In one embodiment, the composition is formulated for transdermal administration. Administration is further described in the "Routes and Forms of Administration" section, below.

In embodiments of the invention, the composition can include a compound that enhances the effect of copper compounds in reducing or alleviating conditions and diseases associated with exposure to toxins, such as pore-forming toxins (PFTs). The compound can be one that is commonly or generally recognized as safe (GRAS) for use. Non-limiting examples of compounds that can be employed in the disclosed compositions include, but are not limited to, d-lactulose, magnesium sulfate, urea, vinegar, lanolin, triclocarban, and the like.

In embodiments of the invention, the additional compound can be found in the compositions as disclosed herein in an amount ranging from about 0.0005% (w/v) to about 95% (w/v). In some embodiments, the additional compound can be found in the disclosed compositions in amount ranging from about 0.001% (w/v) to about 85% (w/v). In some embodiments, the additional compound can be found in the disclosed compositions in amount ranging from about 0.01% (w/v) to about 75% (w/v). In some embodiments, the additional compound can be found in the disclosed compositions in amount ranging from about 0.1% (w/v) to about 65% (w/v). In some embodiments, the additional compound can be found in the disclosed compositions in amount ranging from about 1.0% (w/v) to about 55% (w/v). In some embodiments, the additional compound can be found in the disclosed compositions in amount ranging from about 5% (w/v) to about 45% (w/v). In some embodiments, the additional compound can be found in the disclosed compositions in amount ranging from about 10% (w/v) to about 35% (w/v). In some embodiments, the additional compound can be found in the disclosed compositions in amount ranging from about 20% (w/v) to about 25% (w/v). Acceptable amounts include ranges and amounts within the recited ranges, including endpoints.

D-lactulose can substantially inhibit hemolytic toxins and thus substantially reduce morbidity and mortality. In particular, a dramatic absence of hemolysis was observed in the presence of 10 mM d-lactulose (Chung, J. J., Ratnapala, L. A., Cooke, I. M., Yanagihara, A. A., Toxicon 39 (2001) 981-990, which is incorporated herein by reference in its entirety). In some embodiments, a composition as disclosed herein comprises d-lactulose. Thus, in some embodiments, d-lactulose can be found in the disclosed compositions in amount ranging from about 0.5% (w/v) to about 25% (w/v). In some embodiments, d-lactulose can be found in the disclosed compositions in amount ranging from about 1.0% (w/v) to about 15% (w/v). In some embodiments, d-lactulose can be found in the disclosed compositions in amount ranging from about 2.0% (w/v) to about 10% (w/v). In some embodiments, d-lactulose can be found in the disclosed compositions in amount ranging from about 4.0% (w/v) to about 5.0% (w/v). Acceptable amounts include ranges and amounts within the recited ranges, including endpoints.

Magnesium sulfate can inhibit self-assembly for formation of a pore. Magnesium sulfate also has the added benefit of being soluble in aqueous solutions and inexpensive as a reagent. In some embodiments, a composition as disclosed herein comprises magnesium sulfate. In some embodiments, magnesium sulfate can be found in the disclosed compositions in amount ranging from about 0.5% (w/v) to about 30% (w/v). In some embodiments, magnesium sulfate can be found in the disclosed compositions in amount ranging from about 1.0% (w/v) to about 25% (w/v). In some embodiments, magnesium sulfate can be found in the disclosed compositions in amount ranging from about 2.0% (w/v) to about 20% (w/v). In some embodiments, magnesium sulfate can be found in the disclosed compositions in amount ranging from about 5.0% (w/v) to about 15% (w/v). Acceptable amounts include ranges and amounts within the recited ranges, including endpoints.

Urea is a well-established protein-denaturing agent that is safe for topical use. In some embodiments, a composition as disclosed herein comprises urea. In some embodiments, urea can be found in the disclosed compositions in amount ranging from about 5.0% (w/v) to about 90% (w/v). In some embodiments, urea can be found in the disclosed compositions in amount ranging from about 10% (w/v) to about 80% (w/v). In some embodiments, urea can be found in the disclosed compositions in amount ranging from about 15% (w/v) to about 70% (w/v). In some embodiments, urea can be found in the disclosed compositions in amount ranging from about 20% (w/v) to about 60% (w/v). In some embodiments, urea can be found in the disclosed compositions in amount ranging from about 30% (w/v) to about 50% (w/v). In some embodiments urea is covalently modified. Acceptable amounts include ranges and amounts within the recited ranges, including endpoints.

Vinegar (acetic acid) is a well-established agent for removing jellyfish tentacles and/or treating stings by jellyfish and other animals that is safe for topical use. In some embodiments, a composition as disclosed herein comprises vinegar. In some embodiments, vinegar can be found in the disclosed compositions in amount ranging from about 0% (v/v) to about 90% (v/v). In some embodiments, vinegar can be found in the disclosed compositions in amount ranging from about 5% (w/v) to about 80% (w/v). In some embodiments, vinegar can be found in the disclosed compositions in amount ranging from about 10% (w/v) to about 70% (w/v). In some embodiments, vinegar can be found in the disclosed compositions in amount ranging from about 20% (w/v) to about 60% (w/v). In some embodiments, vinegar can be found in the disclosed compositions in amount ranging from about 30% (w/v) to about 50% (w/v). In a preferred embodiment, the composition does not comprise vinegar. In one embodiment, vinegar is added to the composition (e.g. concentrated composition) immediately prior to use. Acceptable amounts include ranges and amounts within the recited ranges, including endpoints.

Some embodiments can include the use of triclocarban (TCC) in the methods and compositions described herein. Triclocarban can be used alone in the methods of treatment or in combination with the other agents described herein, including without limitation the various copper containing compounds, and the other agents described above and below (e.g., d-lactulose, magnesium sulfate, urea, lanolin and the like). Cnidarian stings by coral, anemone, jellyfish and box jellyfish represent a formidable marine hazard which often results in blistering inflammation after a sting. TCC, a potent epoxide hydrolase inhibitor, has been found to dramatically resolve blistering inflammation within 90 minutes the application of a live jelly in a sting test. Cubozoan venom has been discovered to contain complex lipase activities which show some functional homology to epoxide hydrolase. The post envenomation inflammation has been considered to be an outcome of the slower but potent cnidarian lipase activities. In one non-limiting experiment, the use of 1% TCC in vanacreme, a typical pharmaceutical carrier was tried in an effort to assess the efficacy of TCC to address non porin associated inflammations. The topical agent worked remarkably well fully resolving the blistering inflammation that in the untreated test lasted for up to 72 hr. There is no current primary treatment at the root cause of post envenomation inflammation and blistering. Cortisone and diphenhydramine have been used but these are symptomatic therapies not authentic therapeutic interventions aimed at the root cause.

In one embodiment, TCC is present in the composition at an amount of between about 0.001% and about 10% (w/v). In one embodiment, TCC is present in the composition at an amount of between about 0.01% and about 10%. In one embodiment, TCC is present in the composition at an amount of between about 0.1% and about 10%. In one embodiment, TCC is present in the composition at an amount of between about 1% and about 10%. In one embodiment, TCC is present in the composition at an amount of between about 0.1% and about 5%. In a preferred embodiment, TCC is present in the composition at an amount of between about 0.5% and about 5%. Acceptable amounts include ranges and amounts within the recited ranges, including endpoints. In one embodiment, TCC is not present in the composition.

In some embodiments, the composition comprises triamcinolone acetonide. Preferably, the composition comprising triamcinolone acetonide is formulated for topical administration. In one embodiment, triamcinolone acetonide is present in the composition at an amount of between about 0.01% and about 3% (w/v). In one embodiment, triamcinolone acetonide is present in the composition at an amount of between about 0.01% and about 1% (w/v). In one embodiment, triamcinolone acetonide is present in the composition at an amount of between about 0.01% and about 0.5% (w/v). In one embodiment, triamcinolone acetonide is present in the composition at an amount of between about 0.01% and about 0.2% (w/v). In one embodiment, triamcinolone acetonide is present in the composition at an amount of about 0.1% (w/v). In one embodiment, triamcinolone acetonide is present in the composition at an amount of about 0.025% (w/v). Acceptable amounts include ranges and amounts within the recited ranges, including endpoints. In one embodiment, triamcinolone acetonide is not present in the composition.

In some embodiments, the composition comprises diphenhydramine. In a preferred embodiment, the composition comprising diphenhydramine is formulated for oral, topical, or parenteral administration. In one embodiment, diphenhydramine is present in the composition at an amount of between about 0.1% and about 5% (w/v). In one embodiment, diphenhydramine is present in the composition at an amount of between about 0.1% and about 3% (w/v). In one embodiment, diphenhydramine is present in the composition at an amount of between about 1% and about 2% (w/v). In one embodiment, diphenhydramine is present in the composition at an amount of between about 1 mg and about 500 mg. In one embodiment, diphenhydramine is present in the composition at an amount of between about 5 mg and about 500 mg. In one embodiment, diphenhydramine is present in the composition at an amount of between about 10 mg and about 500 mg. In one embodiment, diphenhydramine is present in the composition at an amount of between about 1 mg and about 100 mg. In one embodiment, diphenhydramine is present in the composition at an amount of between about 1 mg and about 50 mg. In one embodiment, diphenhydramine is present in the composition at an amount of between about 10 mg and about 50 mg. In one embodiment, diphenhydramine is present in the composition at an amount of between about 25 mg and about 50 mg. Acceptable amounts include ranges and amounts within the recited ranges, including endpoints. In one embodiment, diphenhydramine is not present in the composition.

In some embodiments, the composition comprises lidocaine. In a preferred embodiment, the composition comprising lidocaine is formulated for topical administration. In one embodiment, lidocaine is present in the composition at an amount of between about 0.1% and about 10% (w/v). In one embodiment, lidocaine is present in the composition at an amount of between about 0.1% and about 8% (w/v). In one embodiment, lidocaine is present in the composition at an amount of between about 0.1% and about 6% (w/v). In one embodiment, lidocaine is present in the composition at an amount of between about 0.1% and about 5% (w/v). In one embodiment, lidocaine is present in the composition at an amount of between about 0.1% and about 4% (w/v). In one embodiment, lidocaine is present in the composition at an amount of between about 0.5% and about 5% (w/v). Acceptable amounts include ranges and amounts within the recited ranges, including endpoints. In one embodiment, lidocaine is not present in the composition.

It is to be understood that the concentrations recited herein are final concentrations (i.e. concentration to be administered to a subject). In some embodiments, the composition is a concentrated form, in which event the concentrations within the concentrated composition will be higher, depending on the desired final dilution.

Dosage

The dosage administered will vary depending upon known factors, such as the pharmacodynamic characteristics of the particular agent; the age, health and weight of the recipient; the nature and extent of the symptoms; concurrent treatment; the frequency of treatment; and the effect desired. In addition, an effective amount of a composition as disclosed herein will depend, at least, on the particular method of use, the subject being treated, the severity of the affliction, and the manner of administration of the composition. A "therapeutically effective amount" of a composition is a quantity of a composition as disclosed herein sufficient to achieve a desired effect in a subject (host) being treated. For example, this can be the amount of a composition necessary to prevent, inhibit, reduce or relieve a condition caused by a toxin such as a pore-forming toxin as disclosed herein.

Therapeutically effective doses of a disclosed composition can be determined by one of skill in the art. The amount of the composition that is effective in the treatment or prevention of a condition associated with a pore-forming toxin can be determined by standard clinical techniques well known to those of skill in the art. In addition, in vitro or in vivo assays can optionally be employed to help identify optimal dosage ranges. One of ordinary skill in the art will readily be able determine an approximate or precise dose to be employed.

Formulations

In some aspects of the invention, a therapeutic treatment is provided, the treatment comprising the use of a composition as disclosed herein, which can be a pharmaceutical composition or therapeutic agent containing the same, or a pharmaceutically acceptable salt or solvate thereof, and at least one pharmaceutical carrier or diluent. The composition or agent can be used in the prophylaxis and/or treatment of the foregoing diseases or conditions and in therapies as disclosed herein. In some embodiments, the carrier is a pharmaceutically acceptable carrier and is compatible with, i.e. does not have a deleterious effect upon, the other ingredients in the composition. The carrier can be a solid or liquid and can be formulated as a unit dose formulation, for example, as a single-use application that can contain from about 0.0005% to about 50% by weight of the active ingredient.

In some embodiments, the composition as disclosed herein is present in the pharmaceutical composition or therapeutic agent in an amount ranging from about 0.5 percent to about 90 percent by weight of the pharmaceutical composition or therapeutic agent. In some embodiments, the composition is present in an amount ranging from about 1 percent to about 85 percent by weight of the pharmaceutical composition or therapeutic agent. In some embodiments, the composition is present in an amount ranging from about 5 percent to about 80 percent by weight of the pharmaceutical composition or therapeutic agent. In some embodiments, the composition is present in an amount ranging from about 10 percent to about 75 percent by weight of the pharmaceutical composition or therapeutic agent. In some embodiments, the composition is present in an amount ranging from about 15 percent to about 50 percent by weight of the pharmaceutical composition or therapeutic agent. In some embodiments, the composition is present in an amount ranging from about 25 percent to about 35 percent by weight of the pharmaceutical composition or therapeutic agent. Acceptable amounts include ranges and amounts within the recited ranges, including endpoints.

In some embodiments, the composition as disclosed herein is present in an amount ranging from about 2 percent to about 25 percent by weight of the pharmaceutical composition or therapeutic agent. In some embodiments, the composition is present in an amount ranging from about 2 percent to about 20 percent by weight of the pharmaceutical composition or therapeutic agent. In some embodiments, the composition is present in an amount ranging from about 2 percent to about 10 percent by weight of the pharmaceutical composition or therapeutic agent. In some embodiments, the composition is present in an amount ranging from about 5 percent to about 15 percent by weight of the pharmaceutical composition or therapeutic agent. In some embodiments, the composition is present in an amount ranging from about 5 percent to about 10 percent by weight of the pharmaceutical composition or therapeutic agent. Acceptable amounts include ranges and amounts within the recited ranges, including endpoints.

In some embodiments, this disclosure relates to concentrated formulations of the compositions described herein. A concentrated formulation may be diluted with any appropriate excipient. In one embodiment, the excipient used to dilute the concentrated formulation is water. A concentrated formulation may be about 2 times to about 1000 times concentrated. That is, the concentrated formulation is diluted between 1:2 and 1:1000 with the excipient in order to achieve a final concentration that is appropriate for administration to a subject. In one embodiment, the concentrated formulation is about 2 times to about 500 times concentrated. In one embodiment, the concentrated formulation is about 2 times to about 200 times concentrated. In one embodiment, the concentrated formulation is about 2 times to about 100 times concentrated. In one embodiment, the concentrated formulation is about 2 times to about 50 times concentrated. In one embodiment, the concentrated formulation is about 2 times to about 10 times concentrated. In one embodiment, the concentrated formulation is about 10 times to about 500 times concentrated. In one embodiment, the concentrated formulation is about 50 times to about 500 times concentrated. In one embodiment, the concentrated formulation is about 100 times to about 500 times concentrated. In one embodiment, the concentrated formulation is about 200 times to about 500 times concentrated. Acceptable amounts include ranges and amounts within the recited ranges, including endpoints.

Methods of the Invention

The methods of treatment of the present invention include methods that are administered to a subject in need thereof. As used herein, "subject," may refer to any living creature, typically an animal, preferably a mammal, and more preferably a human.

In one aspect of the invention is provided a method for treating exposure to a pore forming toxin in a subject, the method comprising administering to the subject a therapeutically effective amount of a composition comprising copper, wherein a symptom or condition of the exposure is treated. In one embodiment, a composition as described above is administered. In one embodiment, the pore forming toxin is from cnidarian venom, sea urchin venom, coral venom, insect venom, plant venom, serpent venom, or a pathogenic virus or bacterium. In one embodiment, the toxin is from a jellyfish. In one embodiment, the toxin is from a fire ant. In one embodiment, the toxin is from a bacterium. In one embodiment, bacterial sepsis is treated.

The composition may be administered by any route, as described below. In one embodiment, the composition is administered topically. In one embodiment, the composition is administered intravenously.

Routes and Forms of Administration

In embodiments of the invention, a composition as disclosed herein can be administered topically or transdermally. Additional routes of administration include intravenous, intramuscular, oral, sublingual, buccal, parenteral (including, for example, subcutaneous, intramuscular, intra-arterial, intraperitoneal, intracisternal, intravesical, intrathecal, or intravenous), and rectal points of entry. Such routes of administration can be optimized according to the applicable clinical scenario. In one embodiment, the composition is not administered by intramuscular injection. In one embodiment, the composition is not administered by intrathecal injection.

In embodiments of the invention, the therapeutic composition is administered topically. In some embodiments, topical administration of the therapeutic composition is accompanied by application of heat to increase dermal adsorption. Heat can be applied by, for example, immersion of the affected area in hot water subsequent to topical administration of the composition. In some embodiments, heat is applied by immersion in heated water of up to 45° C. for at least 5 minutes. In some embodiments, heat is applied by immersion in heated water of up to 45° C. for at least 10 minutes. In some embodiments, heat is applied by immersion in heated water of up to 45° C. for at least 15 minutes. In some embodiments, heat is applied by immersion in heated water of up to 45° C. for at least 20 minutes. In some embodiments, heat is applied by immersion in heated water of up to 45° C. for at least 30 minutes. In some embodiments, heat is applied by immersion in heated water of up to 45° C. for at least 45 minutes. In some embodiments, heat is applied by immersion in heated water of up to 45° C. for at least 60 minutes. In some embodiments, no heat is applied.

In embodiments of the invention, the therapeutic composition is administered transdermally. In one embodiment, the composition is applied to the drug electrode of an iontophoresis unit, and the drug electrode and ground electrode are applied to the skin of a subject in need of treatment. Voltage is then applied to deliver the compound transdermally to the subject. Typical composition concentrations applied to the drug electrode range from about 0.001 mM to about 250 mM, from about 0.05 mM to about 200 mM, from about 0.1 mM to about 100 mM, from about 1 mM to about 50 mM, or from about 5 mM to about 25 mM. Typical voltages applied to the skin of the subject range from about 0.1 mAmp/min to about 80 mAmp/min. An appropriate voltage amount is one that alleviates symptoms associated with exposure to a pore-forming toxin and improves medical outcome for the subject while maintaining the comfort level of the subject being treated. Acceptable amounts include ranges and amounts within the recited ranges, including endpoints.

Formulations suitable for transdermal administration can be prepared for delivery by transdermal patches with or without electrophoretic current to augment diffusion or deliver agent. Transdermal administration can be also by use of "nanoneedles". (see Escobar-Chávez J J, Bonilla-Martínez D, Villegas-González M A, Revilla-Vázquez A L. J Clin. Pharm (2009), which is incorporated by reference in its entirety).

Formulations suitable for oral administration can be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Formulations suitable for transmucosal methods, such as by sublingual or buccal administration include lozenges patches, tablets, and the like comprising the active compound and, typically a favored base, such as sugar and acacia or tragacanth and pastilles comprising the active compound in an inert base, such as gelatin and glycerine or sucrose acacia.

Formulations suitable for parenteral administration typically comprise sterile aqueous solutions containing a predetermined concentration of the copper composition and possibly another therapeutic agent; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions may also be suitable for formulations for parenteral administration. Although such solutions are preferably administered intravenously, they may also be administered by subcutaneous or intramuscular injection.

In addition to the ingredients specifically mentioned above, the formulations of the present invention can include other agents known to those skilled in the art, having regard for the type of formulation in issue. For example, formulations suitable for oral administration can include flavoring agents and formulations suitable for intranasal administration may include perfumes.

In some embodiments, the therapeutic composition is used as a prophylactic treatment prior to a subject coming in contact with an agent that causes the reactions, symptoms or conditions disclosed herein. In some embodiments, the therapeutic composition is used as a topical or oral prophylactic treatment prior to a subject encountering a cnidarian. In some embodiments, the therapeutic composition is used as a topical or oral prophylactic treatment prior to a subject encountering a fire ant.

In some embodiments, oral copper gluconate is used as a prophylactic to build up serum levels and provide a protective level of copper within the body prior to a potential exposure to PFTs or MPs.

Suitable pharmaceutical carriers are described in Remington's Pharmaceutical Sciences, Mack Publishing Company, a standard reference text in this field.

Amounts of exemplary, non-limiting compounds that may be present in the composition are provided in Table 1. These amounts are provided as a general guide only, and are not intended to be limiting. Additional active and/or inert ingredients may be present in the composition.

EXAMPLES

The following Examples are intended to further illustrate certain embodiments of the disclosure and are not intended to limit its scope.

Example 1

Copper Gluconate Effect on Fire Ant Venom-induced Hemolysis

The membrane disruptive potential of ant venom protein was determined by incubating 1-2% human red blood cells (RBCs) with increasing amounts of fire ant venom (*Solenopsis invicta*) for 3 min, 15 min, 30 min, 1 hour, and 3 hours at 37° C. The results are depicted in FIG. 1. The $HU_{50}$ (Hemolytic Unit) is approximately 37 microgram per milliliter per 1% RBCs (37 µg/mL/%). This is about 1/1000th the potency of box jellyfish venom. $HU_{50}$ refers to the dose at which 50% of the RBCs in a 1% solution were lysed at one hour at 37° C.

Figure 2:
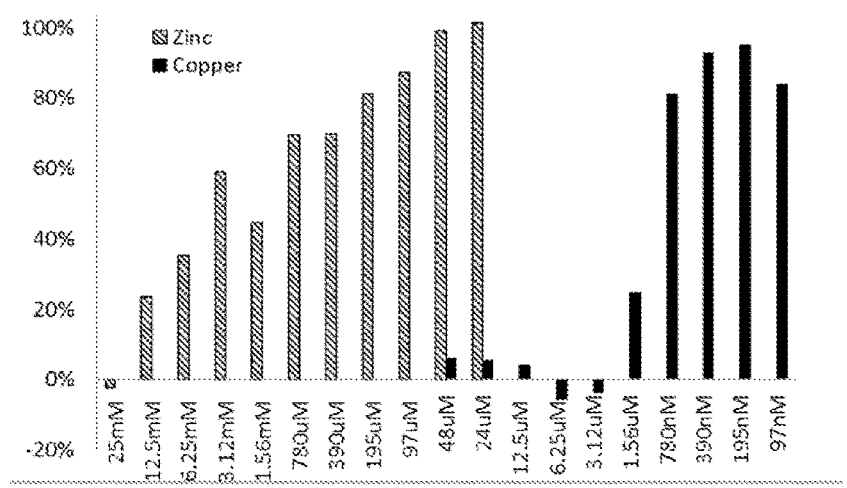
FIG. 2 depicts zinc and copper gluconate inhibition of ant venom induced hemolysis of human red blood cells (RBCs) after a 20 hr exposure at 37° C.

RBCs were incubated with 30 µg/mL fire ant venom and the indicated amount of zinc gluconate or copper gluconate at 37° C. for 20 hours. The results are shown in FIG. 2. The efficacy of copper gluconate is approximately 10,000 times more than zinc gluconate in the inhibition of ant venom (3 µM versus 25 mM). It was determined that copper gluconate is active at approximately 3 µM or greater for fire ant venom inhibition, whereas zinc gluconate is active at approximately 25 mM or greater. Interestingly, zinc gluconate potently stimulated hemolysis at early time points (data not shown). This pharmacokinetic is consistent with the presence of a cytolytic zinc activated phospholipase in ant venom and is a counter-indication for the use of zinc as a therapeutic.

Figure 3:
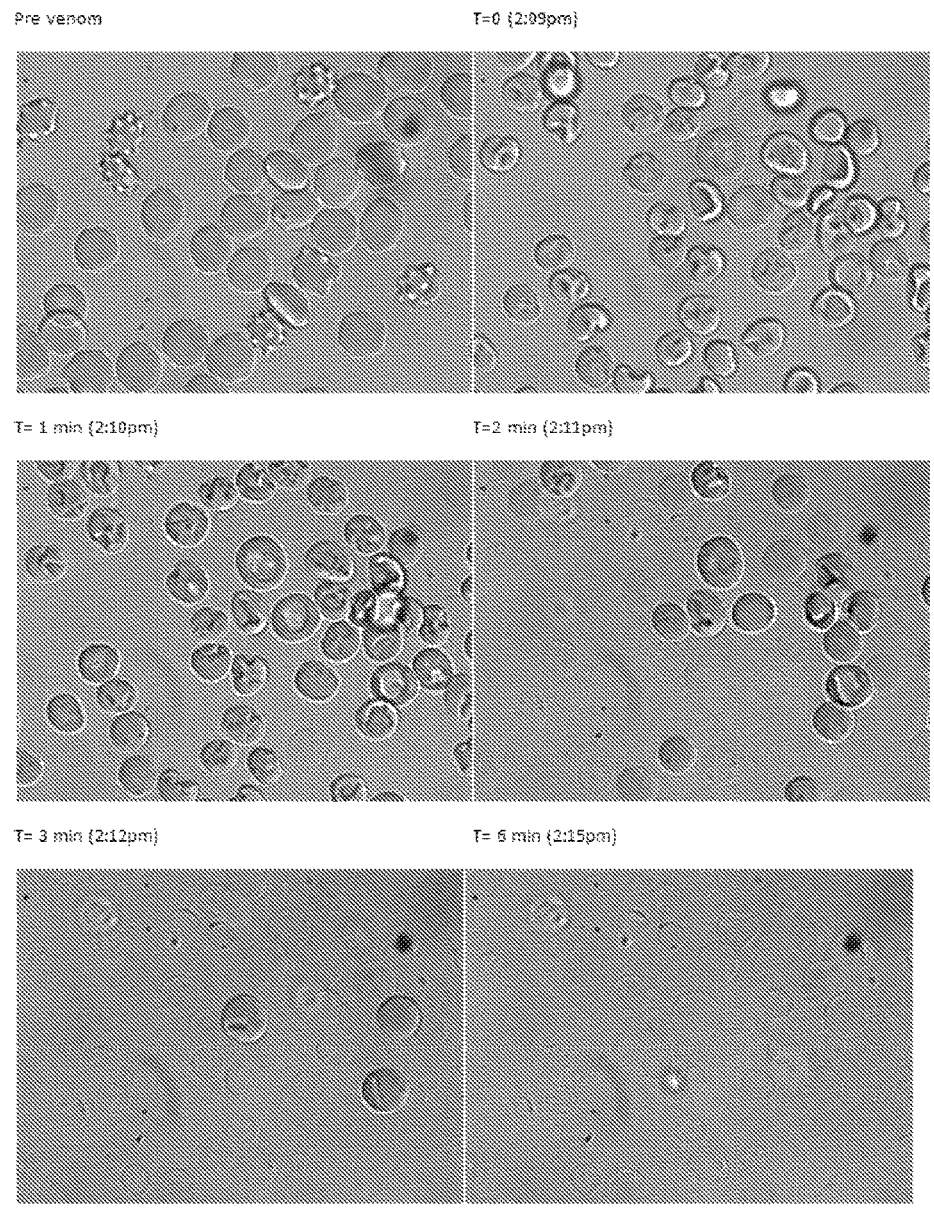
FIG. 3 is a time series light micrographic representation of fire ant venom (10 ng/µL) effects on human RBCs at 37° C.
Figure 4:
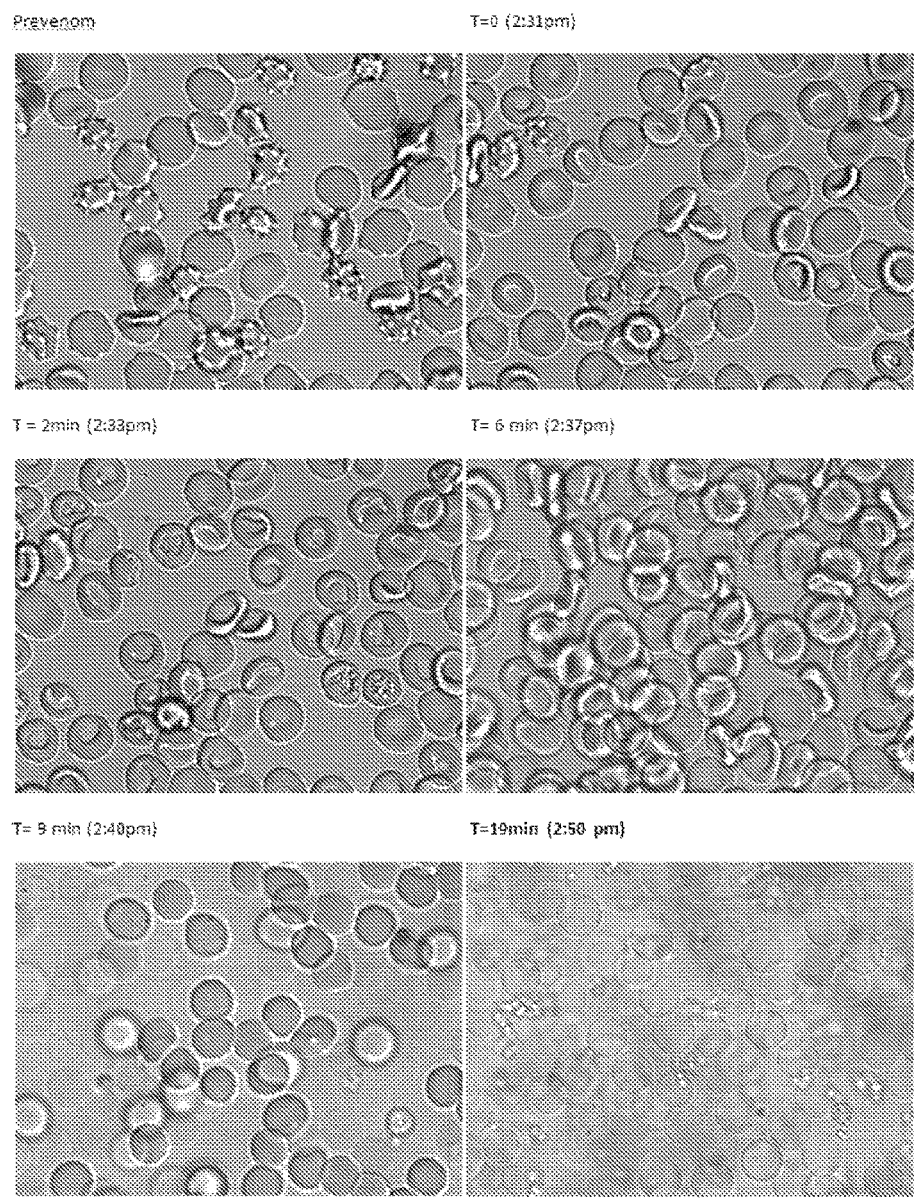
FIG. 4 is a photographic representation of the effect of copper gluconate on fire ant venom-induced hemolysis of RBCs.
Figure 5:
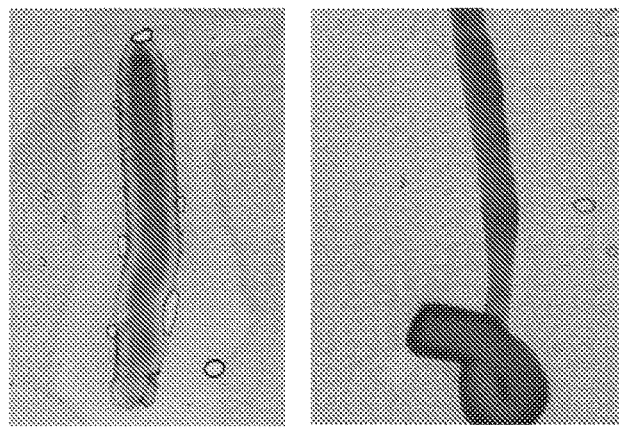
FIG. 5 is a photographic comparison of blood agar clear zones of hemolysis after incubation at 37° C. for 1 hour in response to live tentacle placement in the absence (left) or presence (right) of 10 μM copper gluconate.
Figure 6A:
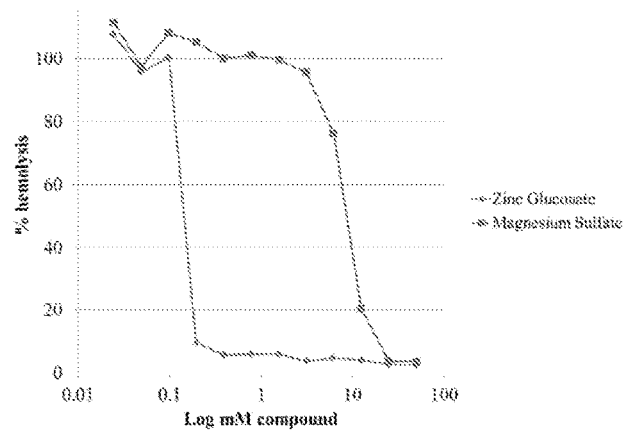
FIG. 6A depicts a dose response curve for inhibition of box jellyfish venom induced hemolysis by zinc gluconate or magnesium sulfate at 37° C. for 1 hour.
Figure 6B:
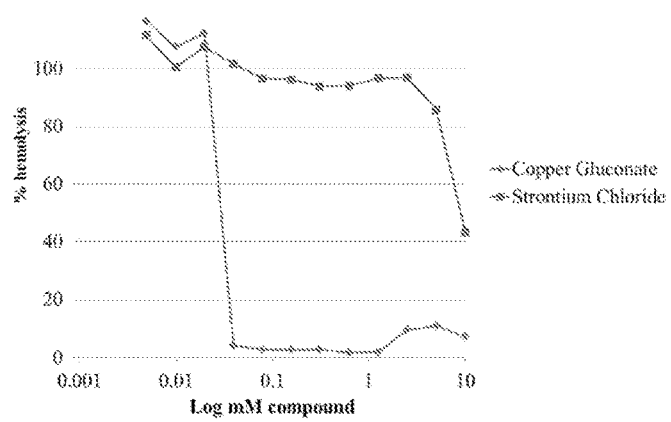
FIG. 6B depicts a dose response curve for inhibition of box jellyfish venom induced hemolysis by copper gluconate or strontium chloride at 37° C. for 1 hour.
Figure 6C:
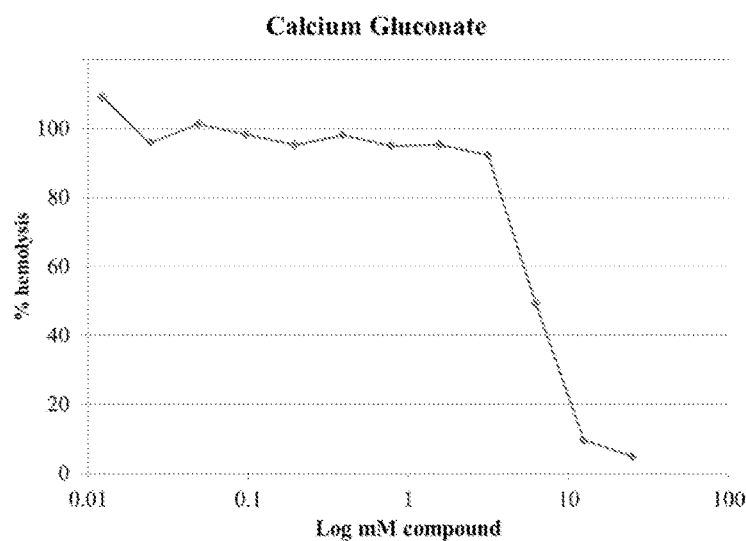
FIG. 6C depicts a dose response curve for inhibition of box jellyfish venom induced hemolysis by calcium gluconate at 37° C. for 1 hour.
Figure 6D:
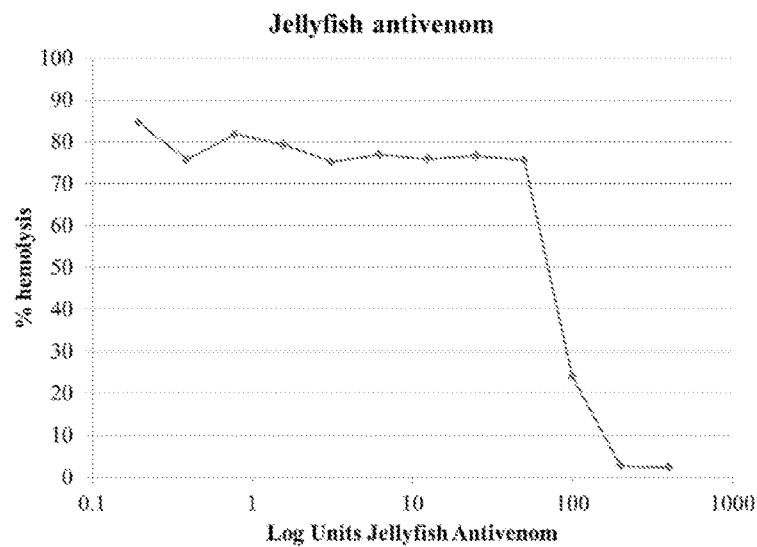
FIG. 6D depicts a dose response curve for inhibition of box jellyfish venom induced hemolysis by jellyfish antivenom at 37° C. for 1 hour.

Live time microscopic imaging comparative studies were also used to examine the effectiveness of copper gluconate. RBCs were incubated with 10 ng/µL fire ant venom alone (FIG. 3), or in combination with 1 µM copper gluconate (FIG. 4) for the amount of time indicated. A single dose of copper gluconate slowed hemolysis by 6 fold.

When a topical blocker solution treatment comprising both zinc and copper (1.6% zinc gluconate, 0.7% copper gluconate, 4.8% urea, 0.4% d-lactulose, 1.3% magnesium sulfate, and Hawaiian soapberry aqueous extract, in anhydrous lanolin) was applied to a fire ant bite, pain scores decreased after administration but redness increased at the site. The increase in site redness may be related to zinc stimulation of one or more phospholipases in ant venom. The pain scores decreased more slowly than would be expected in the absence of zinc-stimulated phospholipases.

Example 2

Copper Gluconate Inhibition of Jellyfish Venom 2-20 mm sections of fresh live *Alatina alata* tentacles were placed on top of freshly prepared RBC agar slide (3% NuSieve GTG low melting agarose, 150 mM NaCl with 2% fresh human RBC). Slides were incubated at 37° C. for one hour. Zones of hemolysis are observed in control slide (FIG. 5, left) but not in slides prepared with 10 μM Copper Gluconate (3% NuSieve GTG low melting agarose, 150 mM NaCl, 10 μM Copper Gluconate with 2% fresh human RBC) (FIG. 5, right). A zone of hemolysis indicates lysis of the red blood cells.

The effect of copper gluconate on jellyfish venom induced hemolysis was evaluated as described in Example 1. Human RBCs were incubated with 5 units/mL/% RBC box jellyfish venom (*Alatina alata*) and zinc gluconate or magnesium sulfate (FIG. 6A), copper gluconate or strontium chloride (FIG. 6B), calcium gluconate (FIG. 6C) or jellyfish anti-venom (FIG. 6D) at increasing doses for 1 hour at 37° C. Samples were centrifuged and the supernatants used to determine OD405. Data is given as percent hemolysis, as determined by OD405 relative to positive control (RBCs incubated with venom). Average negative control value (RBCs with saline and/or inhibitor alone) was approximately 4.8% hemolysis. It was determined that copper gluconate is active at approximately 30 μM or greater for box jellyfish venom inhibition, whereas zinc gluconate is active at approximately 300 μM or greater. Copper gluconate is approximately 10 times more potent than zinc gluconate alone in inhibiting box jellyfish venom.

All references, patent applications and patent publications referred to herein are hereby incorporated by reference in their entireties.

What is claimed is:

1. A composition comprising from about 3 to about 15 μm of copper gluconate to treat exposure to a pore-forming jellyfish or fire and toxin in a subject, wherein the composition does not comprise a zinc containing compound.

2. The composition of claim 1, further comprising at least one of lactulose, magnesium-salt, lanolin, and urea.

3. The composition of claim 2, wherein the composition comprises urea.

4. The composition of any one of claims 1, wherein the composition is formulated for topical administration.

5. The composition of any one of claims 1, wherein the composition is formulated for intravenous administration, oral administration, or intraperitoneal administration.

6. A composition comprising from about 20 to about 90 mM of copper gluconate to treat exposure to a pore-forming jellyfish or fire ant toxin in a subject, wherein the composition does not comprise a zinc containing compound.

7. The composition of claim 6, further comprising at least one of lactulose, magnesium-salt, lanolin, and urea.

8. The composition of claim 7, wherein the composition comprises urea.

9. The composition of claim 6, wherein the composition is formulated for topical administration.

10. The composition of claim 6, wherein the composition is formulated for intravenous administration, oral administration, or intraperitoneal administration.

* * * * *